United States Patent [19]  
Cohen et al.

[11] 4,374,240  
[45] * Feb. 15, 1983

[54] POLYMER COMPOSITIONS COMPRISING HEMIACETALS OF ADDUCTS OF ACROLEIN AND ISOCYANURIC ACID

[75] Inventors: Saul M. Cohen, Springfield; John R. LeBlanc, Wilbraham, both of Mass.

[73] Assignee: Monsanto Company, St. Louis, Mo.

[*] Notice: The portion of the term of this patent subsequent to Oct. 6, 1998, has been disclaimed.

[21] Appl. No.: 219,391

[22] Filed: Dec. 22, 1980

[51] Int. Cl.$^3$ .................... C07D 251/34; C08G 4/00
[52] U.S. Cl. .................... 528/230; 525/185; 525/401; 528/246; 528/254; 528/259
[58] Field of Search ............ 544/221; 528/230, 246, 528/254, 259; 525/185, 401

[56] References Cited

U.S. PATENT DOCUMENTS

| | | | |
|---|---|---|---|
| 2,495,313 | 1/1950 | Bludworth et al. | 260/615 |
| 2,694,732 | 11/1954 | McTeer et al. | 260/602 |
| 2,947,736 | 8/1960 | Lundberg | 544/221 |
| 3,184,438 | 5/1965 | Phillips et al. | 544/221 |
| 3,235,553 | 2/1966 | Saddle | 544/221 |
| 3,485,833 | 12/1969 | Saddle | 544/221 |
| 3,506,660 | 4/1970 | Schneider et al. | 544/221 |
| 4,280,938 | 7/1981 | Strazik et al. | 260/21 |
| 4,281,091 | 7/1981 | Strazik et al. | 525/518 |
| 4,293,461 | 10/1981 | Strazik et al. | 525/518 |
| 4,293,693 | 10/1981 | Cohen et al. | 544/221 |

FOREIGN PATENT DOCUMENTS

| | | |
|---|---|---|
| 962824 | 4/1957 | Fed. Rep. of Germany . |
| 2633685 | 2/1978 | Fed. Rep. of Germany ...... 544/221 |
| 42-9345 | 5/1967 | Japan .................... 544/221 |

OTHER PUBLICATIONS

Kirk-Othmer, Encyclopedia of Chemical Technology, Second Completely Revised Edition, vol. 10, p. 646, Wiley (1966).

*Primary Examiner*—Ronald W. Griffin  
*Attorney, Agent, or Firm*—R. Bruce Blance; William J. Farrington; Paul D. Matukaitis

[57] ABSTRACT

Polymer compositions comprising hemiacetals of acrolein-isocyanuric acid adducts and polyfunctional compounds containing hemiacetal-reactive groups such as amines, amides, alcohols, thiols and oxiranes. The compositions are useful in molding, laminating, coating and adhesive applications.

13 Claims, No Drawings

POLYMER COMPOSITIONS COMPRISING HEMIACETALS OF ADDUCTS OF ACROLEIN AND ISOCYANURIC ACID

This invention relates to polymer compositions comprising polyfunctional hemiacetal-reactive compounds and hemiacetals of acrolein-isocyanuric acid adducts and to the polymeric reaction products of such compositions and to articles comprising such reaction products. In particular this invention relates to polymer compositions comprising polyfunctional hemiacetal-reactive compounds and (3-oxopropyl)isocyanurate hemiacetals and to the polymeric reaction products thereof and to articles comprising such reaction products.

The adducts of isocyanuric acid and acrolein are prepared by addition of isocyanuric acid to the ethylenically unsaturated double bond of acrolein under mildly acid conditions to provide 3-oxopropyl substituents on the nitrogen atoms of the isocyanuric acid. The adducts are formed by addition of at least about 1 mole of acrolein per mole of isocyanuric acid and preferably from about 2 to about 3 moles of acrolein per mole of isocyanuric acid. Hemiacetals of the adducts are formed by reaction with a monohydric primary or secondary alcohol. Preferably from about 0.5 to about 1 mole of monohydric alcohol is reacted per mole of combined acrolein so that at least about half of the acrolein moieties of the adducts are converted to (3-hydrocarbyloxy-3-hydroxypropyl) groups. The compositions of the present invention comprise such hemiacetals and polyfunctional hemiacetal-reactive compounds. The preferred polyfunctional hemiacetal-reactive compounds contain functional groups selected from the group consisting of amine, amide, alcohol, thiol and oxirane. Another aspect of the invention is directed to the polymeric reaction products of the compositions and yet another aspect is directed to articles comprising the polymeric reaction products.

THE PREFERRED EMBODIMENTS

The reaction of acrolein and isocyanuric acid can be carried out by any suitable method which brings acrolein into molecular contact with isocyanuric acid under mildly acid conditions for example by dissolving the isocyanuric acid in a suitable inert solvent and adding acrolein, or by forming a slurry of isocyanuric acid in a mildly acid solvent medium containing acrolein and reacting at a suitable temperature to allow the isocyanuric acid to dissolve and react with the acrolein. At least about one mole of acrolein is reacted with one mole of isocyanuric acid to form an aldehyde containing an average of about one 3-oxopropyl group per isocyanurate ring, hereinafter referred to as the isocyanuric monoaldehyde. Preferably at least about 2 moles of acrolein are reacted with one mole of isocyanuric acid to form an aldehyde containing an average of about two 3-oxopropyl groups per isocyanurate ring, hereinafter referred to as the isocyanuric dialdehyde and more preferably about three moles of acrolein are reacted per mole of isocyanuric acid to provide an aldehyde, containing tris(3-oxopropyl) isocyanurate as the major fraction, hereinafter referred to as the isocyanuric trialdehyde.

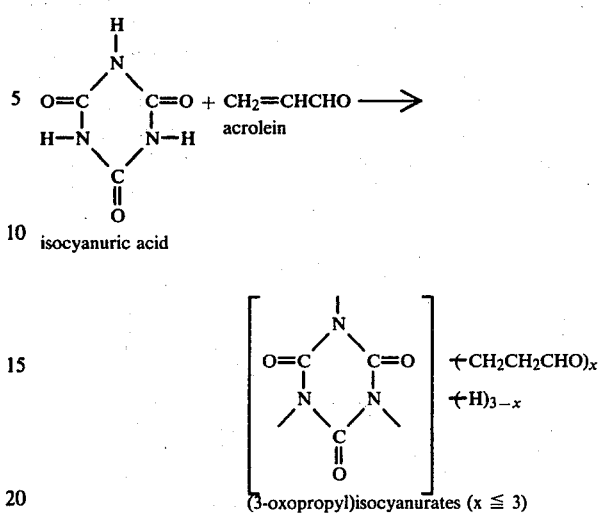

(3-oxopropyl)isocyanurates ($x \leq 3$)

Under normal conditions, isocyanuric acid is the predominant tautomer in "cyanuric acid", comprising about 94 mole percent of the tautomeric mixture. In the reaction with acrolein, the isocyanuric acid tautomer reacts more readily than the cyanuric acid tautomer so that the reaction product may contain more than 94 percent of the isocyanurate derivative. However, to the extent that cyanurates are formed, since they contain an equal number of aldehyde groups, they contribute equally to the aldehyde functionality of the product aldehyde. For the purposes of this disclosure, it is understood that the term "isocyanuric acid" includes isocyanuric acid containing a minor amount of cyanuric acid tautomer.

Several commercial grades of "cyanuric acid" are available, containing various amounts of impurities such as ammelide and ammeline and ammelide- and ammeline-sulfamic acids. While any of these grades are suitable for the addition of acrolein, it is preferred that the "cyanuric acid" contain at least about 98 weight percent of the isocyanuric and cyanuric acid tautomers, and ammelide- and ammeline-sulfamic acids in the range of about 0.1 to about 0.3 weight percent.

The reaction of isocyanuric acid with acrolein can be carried out at any temperature which allows a reasonable rate of reaction. In the solution process this temperature is preferably selected in the range from room temperature to about 120° C. In the slurry process the temperature range is preferably selected in the range of about 50° to about 120° C. to obtain an appreciable rate of solution of the isocyanuric acid and interaction with the acrolein. More preferably in the slurry process the reaction temperature is selected in the temperature range of about 80° to about 100° C. The most preferred range is about 88° to about 92° C. to achieve a fast rate of reaction without excessive formation of insoluble polymer.

In the solution process for the reaction of isocyanuric acid with acrolein, the solvent can be any inert solvent which allows the pH to be adjusted to the range of about 5 to about 7. In the slurry process the solvent medium can be acrolein in substantial excess over the stoichiometric amount for reaction with isocyanuric acid, or it can be selected from the group of solvents for the aldehyde reaction product which are inert to aldehydes under the conditions of the reaction, and can optionally contain an excess of acrolein over the amount desired to be added to the isocyanuric acid. Excess acrolein can be used, especially when a high degree of acrolein addition and a fast reaction rate are desired. Thus, depending upon the desired degree of acrolein addition, the amount of acrolein can range from about 1 mole to about 6 moles or more per mole of isocyanuric acid. In general the range of solvents for the isocyanuric monoaldehyde is rather limited and includes solvents such as water, dimethylformamide, dimethylacetamide and methyl sulfoxide which are inert but highly polar. In contrast the range of solvents for the isocyanuric trialdehyde is quite broad and includes ethers, esters, ketones and hydrocarbons or mixtures thereof. Among the preferred solvents for the trialdehyde are the lower boiling ethers, esters and ketones since they can be readily evaporated when the reaction is complete.

The term "mildly acid conditions" as used herein is meant to describe a reaction medium of pH in the range of about 5 to about 7. pH is measured by applying a few drops of reaction solution to universal pH paper or some comparable pH color indicator, allowing the solvent to evaporate and adding a few drops of methanol to the pH paper. When the methanol has evaporated, the color of the pH paper is compared with the color standard and the pH value thus obtained is considered to be the pH of the reaction solution.

Preferably the pH is maintained in the range of about 5 to about 7 by addition of an amine salt of an amine of $pK_b$ in the range of about 3.5 to about 9.5 and an acid of $pK_a$ in the range of about 1 to about 5.

As will be evident from well-established principles, the quantity of acid required for control of the acidity within the specified limits will be at least that required to react with all the amine plus an amount in excess thereof sufficient to keep the apparent pH of the reaction mixture below 7.0. As will also be evident from well-established principles, the amount of acid to be employed over and above that required for reaction with the amine will vary from acid to acid and amine to amine, dependent upon the dissociation constants of the compounds involved. Thus, in the case of a very weak amine and a strong acid, a slight amount of the acid over the stoichiometric equivalent would be sufficient. Conversely, with a strong amine base and weak acid, stoichiometric equivalents of acid to amine as high as 3 to 1 may be indicated. In the case of the amphoteric amine compounds, the use of acid can be dispensed with, but it is not necessary to do so provided the quantity used is sufficient to take the pH of the reaction outside the specified range. In some instances the use of a small quantity of acid with the amphoteric amine compound also may be found advantageous.

The amine can be selected from primary, secondary and tertiary amines, polyamines, and the like, including amphoteric amine compounds. These amines can be aliphatic or aromatic or mixed aliphatic and aromatic, including carbocyclic and heterocyclic. By the term "amphoteric amine compound", as used herein, is meant an amine of the classes listed above which also contains in the molecule an acidic hydrogen atom connected to a carbon atom through an oxygen atom, as in the case of the aminoacids and aminophenols by way of illustration. Representative of the useful amines are the following: monomethylamine, dimethylamine, trimethylamine, monoethylamine, diethylamine, triethylamine, monopropylamine, dipropylamine, tripropylamine, monobutylamine, dibutylamine, tributylamine, and mono-, di-, and tri-alkyl amines containing up to seven carbon atoms to the alkyl group; aniline, diphenylamine, toluidine, monomethylaniline, dimethylaniline and other arylamines and alkyl-substituted arylamines containing up to seven carbon atoms to the group attached to the nitrogen atom; monoethanolamine, diethanolamine, triethanolamine, diethylene triamine, triethylene tetramine, phenylenediamines, and other aliphatic and aromatic polyamines containing not more than seven carbon atoms to the aliphatic or aromatic group present therein. Representative of the amphoteric amine compounds that can be used as catalyst in our process are glycine, beta-alanine, anthranilic acid, aminophenols and the like.

The acid can be selected from a wide variety of acids including formic, acetic, propionic, butyric, valeric, hexanoic, heptanoic, octanoic, oxalic, succinic, glycolic, lactic, benzoic, phthalic, sulfamic and the like.

In general, the preferred amines are tertiary amines such as trimethylamine, triethylamine and tripropylamine and the preferred acids are the lower carboxylic acids such as formic acid, glycolic acid and lactic acid.

The amine salt concentration is not narrowly critical but may be varied within moderate limits. A concentration in the range of about 0.1 to about 1.0 mole per hundred moles of isocyanuric acid is preferred. Within this range the exact amount employed depends to some extent on the particular amine salt selected and the reaction temperature. At concentrations below about 0.1 mole of amine salt per 100 moles of isocyanuric acid, an undesirable formation of acrolein oligomers competes with the formation of the desired adduct of isocyanuric acid, and crosslinked product also forms.

When the reaction has been carried to completion, the amine salt can be removed by treatment of the reaction solution with a suitable adsorbent or absorbent for the amine salt such as a diatomaceous earth, finely divided silica, alumina, animal charcoal, an ion-exchange resin or a combination of ion-exchange resins. The treatment can be carried out in any convenient way, such as by stirring the solution with the sorbent for sufficient time to substantially sorb the amine salt and filtering off the sorbent, or by passing the reaction solution through a bed of sorbent. After removal of the amine salt, sufficient acid of moderate strength with pKa in the range of about 1 to about 3 may be added to produce a final product with a pH in the range of about 1 to about 3 and more preferably in the range of about 1.5 to 2. Suitable acids include oxalic acid, dichloroacetic acid, glycerophosphoric acid, maleic acid, 2-methyl-6-nitrobenzoic acid and phosphorous acid. The solution of the aldehyde reaction product is then stripped to remove solvent. When the reaction solvent is provided by an excess of acrolein, removal of the excess acrolein is preferably achieved by a multicycle addition of inert solvent and removal of the solvent by vacuum stripping and finally water is added and removed by vacuum stripping. Suitable solvents for the stripping process are ethers, esters and ketones of boiling point in the range of about 60° to about 100° C.

Any commerical grade of acrolein is suitable for the reaction with isocyanuric acid. Such grades generally contain up to about 4 weight percent water. Also from about 0.1 to about 0.25 weight percent hydroquinone can be present as a polymerization inhibitor. While water up to about 4 percent is tolerable and has little effect on the acrolein-isocyanuric acid reaction, we have found that when the water content is reduced to less than about 1.0 percent, the amount of polyacrolein produced during the reaction is decreased. The tendency of acrolein to dimerize by a Diels Alder addition has long been recognized. Acrolein containing from about 0.1 to about 2.0 percent of dimer yields greater than the theoretical amount of the desired aldehyde upon reaction of the acrolein with isocyanuric acid. However, analysis by thin layer chromatography reveals no difference in the aldehyde prepared from such acrolein compared with aldehyde prepared by reaction of isocyanuric acid and acrolein containing less than 0.1 percent dimer.

In general, the aldehydes of the present invention obtained by addition of at least about one mole of acrolein per mole of isocyanuric acid can be viscous liquids, glasses or crystalline solids at room temperature. The average molecular weight by gel phase chromatography is generally in the range of about 180 to about 2000. When the aldehydes are subjected to aldehyde analysis by the hydroxylamine method, they are found to contain the theoretical amount of aldehyde based on the amount of acrolein added to the isocyanuric acid. Thus they behave as if they consist entirely of monomeric (3-oxopropyl)isocyanurates.

The adduct of three moles of acrolein and one mole of isocyanuric acid is a turbid viscous liquid at temperatures above about 70° C. and sets to a glassy solid at room temperature, with a glass transition temperature in the range of about 60° to about 70° C. The solid becomes opaque and partly crystalline with time and is then readily ground to a white powder. The number average molecular weight of the solid adduct is in the range of about 250 to about 2000. When the adduct is subjected to aldehyde analysis, it behaves as if it were about 100 percent tris(3-oxopropyl)isocyanurate, but when it is subjected to molecular weight analysis by gel phase chromatography, it is found to consist of a major fraction of tris(3-oxopropyl)isocyanurate, a large polymer fraction and small amounts of the di- and mono-substituted aldehydes and polyacrolein oligomers. Freshly made product is soluble in a wide range of solvents including chloroform, acetone and water. Solution in water occurs by warming at 60° to 100° C. However, with extended aging at room temperature, solubility is lost first in chloroform, then in acetone and progressively thereafter in other solvents. Accompanying this solubility loss is a progressive decrease in aldehyde intensity in the infrared spectrum. A sample of the aged product heated at 100° C. for 2 to 5 minutes regenerates the original solubility behavior and the original aldehyde carbonyl intensity in the infrared spectrum. The solubility loss and aldehyde decrease observed with time are believed due to association of some of the aldehyde groups, in a manner similar to the behavior of formaldehyde producing paraformaldehyde or trioxane. The reversibility of the association or oligomerization also is similar to that of the formaldehyde-paraformaldehyde system. A solid state $^{13}C$ NMR spectrum of the aged product displays a band at 90 ppm associated with the —O—C—O—structure. It is therefore understood that, within the context of the present invention, the adducts of acrolein and isocyanuric acid are mixtures of mono-, di- and tri-aldehydes and physical associations or oligomers thereof which in the presence of aldehyde-reactive compounds react as if they are intrinsically monomeric and free of oligomers or molecular associations.

The aldehydes of the present invention can be reacted with any of the wide variety of compounds which are reactive with an aldehyde group. Such compounds include ammonia, primary and secondary amines, primary and secondary amides, hydroxylamine, alcohols, thiols, phenols, oxiranes, hydrogen cyanide, bisulfites, semicarbazide, hydrazine and substituted hydrazines. Also the aldehydes of the present invention are readily oxidized to the corresponding carboxylic acids and reduced to the corresponding alcohols by conventional methods for the oxidation and reduction of aldehydes. The aldehydes are useful as crosslinking agents when they are reacted with multifunctional compounds containing aldehyde-reactive groups such as primary and secondary amines, primary and secondary amides, alcohols, thiols, phenols, anilines and oxiranes. The ratio of aldehyde to polyfunctional compound for effective crosslinking is dependent on the equivalence and functionality of the aldehyde and the polyfunctional compound and can be varied within very wide limits to provide low molecular weight polymers, high molecular weight soluble polymers, lightly gelled highly swellable polymers and densely crosslinked, extremely tough, hard, solvent-resistant polymers.

It will be appreciated that aldehyde groups can be monofunctional or difunctional depending upon the type and placement of the aldehyde-reactive groups with which the aldehyde is reacted and the reaction conditions. Thus the aldehyde group will be monofunctional when it is reacted with a primary amine, or with a polyol with hydroxyl groups in 1,2- or 1,3-placement to one another to form a cyclic acetal, or when the reaction is an addition to the carbonyl group of the aldehyde such as hemiacetalization. On the other hand, the aldehyde group will be difunctional when it reacts with an aldehyde-reactive compound by a condensation reaction, with water being split out as in acetalization of a polyol or mercaptalization of a polythiol. Thus, depending on the reactants and reaction conditions, the isocyanuric monoaldehyde can behave as a monofunctional or difunctional reactant, the isocyanuric dialdehyde can behave as a difunctional or tetrafunctional reactant and the isocyanuric trialdehyde can behave as a trifunctional or hexafunctional reactant. Therefore while the di- and tri-aldehydes, comprising bis- and tris-(3-oxopropyl)isocyanurates as major fractions, will be effective crosslinking or polymerization agents for reactants which are at least difunctional, the monoaldehyde compositions comprising a major fraction of mono(3-oxopropyl)isocyanurate will preferably be used as a crosslinking or polymerization agent only in condensation reactions, such as acetalization.

Since the aldehydes of the present invention are effectively monomeric and behave as if the aldehyde groups are not associated or polymerized when the aldehydes are reacted with compounds containing an aldehyde-reactive group, the mole ratio of aldehyde to polyfunctional aldehyde-reactive compound required for polymerization or crosslinking will be selected in the range of about 1:m/2 to about n/2:1, where m is the number of aldehyde groups per isocyanuric ring when the aldehyde behaves as a monofunctional moiety or is 2 times the number of aldehyde groups per isocyanuric ring when the aldehyde behaves as a difunctional moiety and n is the functionality of the polyfunctional aldehyde-reactive compound, it being understood that m and n must be 2 or more for chain-building reactions.

Suitable polyols for crosslinking reactions with the aldehydes of the present invention include oligomeric and polymeric hydroxy compounds of low, intermediate and high molecular weight containing a plurality of hydroxy groups per molecule, such as hydroxy-containing polyesters and alkyds, polyethers such as polyethylene glycols, polypropylene glycols and polytetramethylene glycols, polyvinyl alcohol and copolymers of vinyl alcohol, polymers of allyl alcohol, polymers of hydroxyacrylates such as 2-hydroxyethyl acrylate and 2-hydroxyethyl methacrylate, starches, starch derivatives, celluloses and cellulose derivatives. Preferably the di- and trialdehydes of the present invention are used since they can provide more efficient crosslinking. Reaction can be carried out under neutral conditions in wataer or in an inert solvent for the reactants to provide hemiacetals or under acid conditions to provide acetals. The temperature of reaction is not critical and is selected preferably in the range of about 80° to about 150° C. to provide the appropriate degree of reaction in a convenient time. Acid catalysts used in acetalization are generally strong acids of pKa less than about 3 such as the mineral acids, oxalic acid, formic acid and acids which are readily soluble in organic systems such as the alkyl-, fluoroalkyl- and arylsulfonic acids and the fluorophosphonic acids. Examples of such acids include methanesulfonic acid, trifluoromethanesulfonic acid, benzenesulfonic acid, p-toluenesulfonic acid and hexafluorophosphoric acid. While the amount of such catalyst is not critical, it is preferably selected in the range of about 0.05 to about 1 weight percent of the composition comprising aldehyde and polyol compound. When reaction conditions are selected to provide hemiacetal, the di- and tri-aldehydes of the present invention can be used to provide polymers from simple polyols such as ethylene glycol, 1,2-propylene glycol, 1,3-propanediol, 1,4-butanediol, 1,6-hexanediol, 1,4-di(hydroxymethyl)-cyclohexane, cyclohexanediols, trimethylolethane, trimethylolpropane, glycerol, pentaerythritol, sorbitol, glucose, sucrose and the like. When the reaction conditions are such that acetals are formed, suitable polyols for polymer formation include those above except diols with hydroxy groups in 1,2- or 1,3-placement such as ethylene glycol and 1,3-propanediol which form cyclic acetals and therefore behave as if they are monofunctional.

Suitable polythiols for reaction with the aldehydes of the present invention include low molecular weight di- and tri-thiols such as 1,2-ethanedithiol, 1,4-butanedithiol, 1,6-hexanedithiol and the like and high molecular weight polythiols such as poly(ethylene thiol), poly(p-styrenethiol) and poly(4-mercaptomethylstyrene).

Among the polyamines which can be reacted with the aldehydes of the present invention are low molecular weight hydrocarbyldiamines and polyamines and poly(hydrocarbylpolyamines) such as 1,2-ethanediamine, 1,6-hexanediamine and 1,12-dodecanediamine, diethylene triamine, tetraethylene pentamine and the like, and intermediate and high molecular weight poly(-hydrocarbylpolyamines), poly(alkylenimines), vinylamine polymers, and the like.

Polyamides suitable for reaction with the aldehydes of the present invention include urea, guanidine, the polyamides of polycarboxylic acids such as adipamide and dimer acid diamide, and high molecular weight polyamides such as the nylons, polypeptides and polyacrylamide.

Polyoxiranes which can be used for reaction with the aldehydes of the present invention include those set forth in the Encyclopedia of Polymer Science and Technology, Wiley 1967, Vol. 6, pp. 212–219 and include the diglycidyl ether of bisphenol-A and oligomers thereof, epoxidized novolacs, aliphatic polyglycidyl ethers, and peracetic epoxidized products such as vinyl cyclohexene dioxide and epoxidized polybutadiene.

The aldehydes of this invention can be converted to monomeric hemiacetals by reaction with a monohydric primary or secondary alcohol. The reaction can be carried out, under mild conditions similar to those for addition of isocyanuric acid to acrolein, merely by contacting the aldehyde with the alcohol if the latter is liquid, or by stirring a mixture of the aldehyde or the alcohol and a solution of the alcohol or the aldehyde in an inert solvent until a clear solution is obtained. Such inert solvents include ethers, esters, and ketones. Preferably the solvent is also a solvent for the hemiacetal product. Since hemiacetal formation is an equilibrium reaction, it can be advantageous to use an excess of the alcohol in forming the hemiacetal. However, when the solid aldehyde is reacted with less than the amount of alcohol needed to cause substantially complete hemiacetalization, a degree of hemiacetalization depending upon the particular monohydric alcohol and its concentration takes place to provide a solution of the partially hemiacetalized isocyanuric aldehyde, stable at room temperature. Mild conditions may be obtained by adding an amine salt to the reaction medium to provide a pH in the range of about 5 to 7, as determined hereinabove for the acrolein-isocyanuric acid reaction medium. The amine salt can be any of those listed hereinabove. The preferred amine salts are prepared from tertiary amines such as trimethylamine, triethylamine and tripropylamine and the lower fatty acids such as formic, acetic and propionic acids. The reaction temperature is not critical and the reaction can be carried out at a temperature selected to provide a reasonable rate of solution of the aldehyde. The reaction temperature is preferably slightly above the glass transition temperature of the aldehyde, for example with the isocyanuric trialdehyde, the temperature is preferably in the range of about 60°–70° C., to obtain rapid solution and avoid possible crosslinking or other undesirable side reactions. When the reaction is complete the amine salt may be removed in the fashion described hereinabove for the preparation of the aldehydes. While any monohydric primary or secondary alcohol or mixture of alcohols may be used in hemiacetalization of the aldehydes of the present invention, the lower boiling $C_1$ to $C_8$ alcohols are preferably selected for the preparation of hemiacetals which are to be used as polymerization or crosslinking agents since such low boiling alcohols may be more readily displaced when the hemiacetals are reacted with polyhydroxy compounds and hence may allow a more rapid rate of cure. Among the preferred alcohols are methyl, ethyl, propyl, isopropyl, butyl, cyclohexyl and benzyl alcohols and 2-alkoxyethanols such as 2-methoxyethanol and 2-butoxyethanol. Methyl alcohol is especially preferred. Since these hemiacetals form stable solutions of low viscosity, they provide a convenient means of incorporating the aldehydes of the present invention as polymerization or curing agents into polyfunctional compounds containing hemiacetal-reactive groups. Since hemiacetal-reactive groups are also aldehyde-reactive, the hemiacetals of monohydric alcohols may be substituted for the parent aldehydes as polymerization or curing agents in the compositions containing the polyfunctional compounds set forth above. Where m is the functionality of the hemiacetal, based on the effective number of hemiacetal and aldehyde groups per isocyanurate ring, the assumption being made that the aldehyde groups behave as if they are not associated or polymerized, and n is the functionality of the hemiacetal-reactive compound, it being a necessary condition that both m and n be about 2 or greater if chain building reaction is to occur, the mole ratio of hemiacetal to polyfunctional compound for effective polymerization or cure is selected in the range of about 1:m/2 to about n/2:1. Of course, the same considerations apply to the functionality of the hemiacetal as to the aldehyde from which it is generated. The hemiacetal groups can be monofunctional or difunctional depending upon the type and placement of the hemiacetal-reactive groups with which the hemiacetal is reacted. Thus the hemiacetal group will be monofunctional when it is reacted with a primary amine, or with a polyol with hydroxyl groups in 1,2- or 1,3-placement to one another to form a cyclic acetal, or when the reaction is limited to a condensation reaction involving the hydroxyl group of the hemiacetal. On the other hand, the hemiacetal group will be difunctional when it reacts with a hemiacetal-reactive compound by condensation reactions in which water and monohydric alcohol are split out as in acetalization of a polyol or mercaptalization of a thiol under strong acid catalysis.

When hemiacetalization of the aldehydes is carried out with excess monohydric alcohol so that hemiacetalization is substantially complete, the equilibrium allows conversion substantially to the corresponding monomeric (3-hydrocarbyloxy-3-hydroxypropyl)isocyanurate. Thus, when the aldehyde reactant is the isocyanuric trialdehyde the product is substantially monomeric tris(3-hydrocarbyloxy-3-hydroxypropyl)isocyanurate. However when the amount of the alcohol is less than sufficient to give substantially complete hemiacetalization of the aldehyde groups of the aldehyde, the hemiacetal comprises a mixture of (3-hydrocarbyloxy-3-hydroxypropyl)isocyanurates, (3-hydrocarbyloxy-3-hydroxypropyl) (3-oxopropyl)isocyanurates, and (3-oxopropyl)isocyanurates. Preferably at least about 0.5 mole of monohydric alcohol is added per mole of combined acrolein for hemiacetal formation.

Crosslinking or polymerization reactions are readily achieved with the hemiacetals of monohydric alcohols by reacting them with polyols under strong acid conditions to produce polyacetals. From what has been said heretofore, the hemiacetals of the monoaldehyde will be effective but the di- and tri-aldehydes are preferred since they can provide more efficient crosslinking. The temperature of reaction is not critical and is selected, preferably in the range of about 80° to about 150° C. to provide the appropriate degree of reaction in a convenient time. Suitable acid catalysts include those listed hereinabove for acetalization of polyols with (3-oxopropyl)isocyanurates. The reaction is carried out in a solvent inert to the reactants. When the polyols are of molecular weight of about 10,000 or less, high solids coating systems can be obtained containing at least about 50 percent solids and more preferably at least about 70 percent solids, the solvent being the monohydric alcohol used in hemiacetalization.

Suitable polyols for the acetalization reaction with the monomeric hemiacetals of the (3-oxopropyl)isocyanurates include oligomeric and polymeric hydroxy compounds containing a plurality of hydroxy groups per molecule, such as hydroxy-containing polyesters and alkyds, polyethers such as polyethylene glycols, polypropylene glycols and polytetramethylene glycols, polyvinyl alcohol and copolymers of vinyl alcohol, polymers of allyl alcohol, polymers of hydroxyacrylates such as 2-hydroxyethyl acrylate and 2-hydroxyethyl methacrylate, starches, starch derivatives, celluloses and cellulose derivatives. Also suitable are the simple polyols such as 1,4-butanediol, 1,6-hexanediol, 1,4-di(hydroxymethyl)cyclohexane, cyclohexanediols, trimethylolethane, trimethylolpropane, glycerol, pentaerythritol, sorbitol, glucose, sucrose and the like. Diols with hydroxy groups in 1,2- or 1,3-placement, such as ethylene glycol and 1,3-propanediol, which form cyclic acetals may be used as monofunctional reactants for control of the molecular weight of the polyacetals.

When the aldehydes of the present invention are reacted with a primary or secondary monohydric alcohol under acid-catalyzed conditions with removal of the water of reaction, acetals are formed. Any monohydric alcohol can be used for the acetal reaction, which is preferably carried out in an inert solvent medium which is a solvent for the acetal of the aldehyde and at least one of the reactants. More preferably, a solvent is selected which allows the water of reaction to be removed by azeotropic distillation. Such solvents include aliphatic and aromatic hydrocarbon solvents such as hexane, heptane, octane, benzene, toluene and xylene, higher boiling alcohols such as butyl alcohol, amyl alcohol, hexyl alcohol and benzyl alcohol and chlorinated hydrocarbons such as chloroform, carbon tetrachloride, ethylenene dichloride and the like. Acid catalysts which may be used are preferably strong acids of $pk_a$ less than 3 such as the mineral acids, oxalic acid and alkyl-, fluoroalkyl- and aryl-sulfonic acids and fluorophosphoric acids, including methanesulfonic acid, trifluoromethanesulfonic acid, benzenesulfonic acid, toluensulfonic acid and hexafluorophosphoric acid. While the amount of acid catalyst is not critical it is preferably selected in the range of about 0.05 to about 1 weight percent of the aldehyde. The temperature of reaction is not critical and is generally determined by the boiling point of the reaction medium. However higher or lower temperatures can be used by carrying out the reaction in a closed vessel to provide super- or sub-atmospheric conditions. The course of the reaction can be followed by decrease of the aldehyde carbonyl band in the infrared spectrum of the isocyanuric aldehyde. When the reaction is complete, the acid catalyst is removed by conventional means for example by neutralization with an inorganic base and filtration of the salt which is formed or by neutralization with an ion exchange resin. Preferred inorganic bases form insoluble salts in the reaction medium and include the oxides and hydroxides of group II A metals, such as magnesium and calcium oxides and hydroxides. While any primary or secondary monohydric alcohol can be used to prepare the acetals of the aldehydes of the present invention, when the acetal is to be used as a polymerization or crosslinking agent for polyfunctional compounds containing acetal-reactive groups such as polyhydroxy compounds, it is preferred to use $C_1$ to $C_8$ alcohols since they can be more readily displaced during the polymerization or crosslinking reaction. Among the preferred alcohols are methyl, ethyl, propyl, isopropyl, butyl, cyclohexyl and benzyl alcohols. The higher boiling alcohols can be used advantageously both as the acetalizing agent and as the azeotropic solvent. More preferably, when the acetal of the aldehyde is to be used as a polymerization or crosslinking agent it is preferred that it be the acetal of methanol. The products of acetalization of the aldehydes with primary or secondary monohydric alcohols are [3,3-di(hydrocarbyloxy)propyl]isocyanurates. Thus acetalization of the trialdehyde with methanol yields an acetal comprising substantially tris(3,3-dimethoxypropyl)isocyanurate. Complete acetalization can be achieved by effecting reaction of about 2 moles of monohydric alcohol per aldehyde group, or about 1 mole of monohydric alcohol per hemiacetal group of the hemiacetal of the aldehyde. The assumption is made that any oligomeric or associated aldehyde reverts to the monomeric or unassociated state, and is consumed in the reaction. Excess of the monohydric alcohol allows the reaction to be completed more rapidly. When less than the stoichiometric quantity of monohydric alcohol for reaction with the aldehyde groups is used in the acetalization reaction, partial acetalization occurs to provide products which nevertheless are more soluble than the aldehydes and hence more amenable to reaction with aldehyde-reactive and acetal-reactive compounds. Preferably at least about 50 percent of the aldehyde groups of the isocyanuric aldehyde are acetalized.

Since the acetals form stable solutions of low viscosity, they provide a convenient means of incorporating the aldehydes of the present invention into polyfunctional compounds containing acetal-reactive groups to effect polymerization or curing of the polyfunctional compounds. Such acetal-reactive groups include hydroxy, mercapto and epoxy groups. Hence the acetals may be substituted for the aldehydes as polymerization or curing agents of the polyfunctional compounds such as the polyhydroxy compounds described above. Polymerizable compositions containing the acetals and the polyfunctional compounds are obtained by blending the acetals and the polyfunctional compounds in the mole ratio of from about 1:m/2 to about n/2:1, where m is the total of acetal, hemiacetal and aldehyde groups per isocyanurate ring of the acetal composition, the aldehyde groups being assumed to be available in the monomeric or unassociated form, and n is the functionality of the polyfunctional compound, both m and n being about 2 or more to achieve chain extension. Like their parent aldehyde groups the acetal groups can act as monofunctional or difunctional groups depending upon the type and placement of the acetal-reactive groups with which the acetal is reacted. Thus the acetal group will be monofunctional when it is reacted with a polyol with hydroxyl groups in 1,2- or 1,3- placement to one another to form a cyclic acetal. On the other hand, the acetal group will be difunctional when it reacts with hydroxy groups which are not in such 1,2- or 1,3-placement to one another.

Crosslinking or polymerization reactions are readily achieved with the acetals of monohydric alcohols by reacting them with polyols under strong acid conditions to produce polyacetals. From what has been said heretofore, it will be appreciated that the monohydric alcohol acetals of the isocyanuric monoaldehyde will be effective for such transacetalizations. However the acetals of the isocyanuric di- and tri-aldehydes are preferred, since they can provide more efficient crosslinking. The temperature of reaction is not critical and is selected, preferably in the range of about 80° to about 150° C. to provide the appropriate degree of reaction in a convenient time. Suitable acid catalysts include those listed hereinabove for acetalization of the aldehydes by monohydric alcohols. The reaction is carried out in a solvent inert to the reactants. When the polyols are of molecular weight of about 10,000 or less, high solids coating systems can be obtained containing at least about 50 percent solids and more preferably at least about 70 percent solids.

Suitable polyols for transacetalization by the acetals formed from the isocyanuric aldehydes and monohydric alcohols include the polyols and the polyhydroxy compounds set forth hereinabove as reactants for the aldehydes and hemiacetals. Diols with hydroxy groups in 1,2- or 1,3-placement such as ethylene glycol and 1,3-propanediol which form cyclic acetals may be used as monofunctional reactants for control of the molecular weight of the polyacetals.

The hemiacetals and acetals of the isocyanuric aldehydes in which substantially complete hemiacetalization or acetalization has been achieved with monohydric alcohols, provide a convenient stable source of essentially monomeric (3-oxopropyl)isocyanurates for reactions in aqueous media since they are readily hydrolyzed when they are added to aqueous media containing a catalytic amount of acid. They are therefore useful for cross linking of polyhydroxy compounds such as polyvinyl alcohol, starch, starch derivatives, cellulose and cellulose derivatives in aqueous solution or dispersion, by acetalization.

The polymerizable compositions comprising polyfunctional compounds and the isocyanuric aldehydes, hemiacetals or acetals of the present invention can be used in a multiplicity of applications. They can be used as adhesives and laminating agents, bonding resins, surface coating systems and molding resins. They can be modified by the addition of pigments, plasticizers, colorants, dyes, pigment dispersing agents, flow control agents, stabilizers and the like.

The following examples are set forth in illustration of the invention and should not be construed as limitations thereof. Unless otherwise indicated, all parts and percentages are by weight.

EXAMPLE 1

Preparation of Isocyanuric Trialdehyde

To a pressure kettle (rated for 500 psi), 526 parts by weight of freshly distilled acrolein containing 100 parts per million 2,6-di-t-butyl-4-methylphenol, 200 parts per million hydroquinone and 100 parts per million formic acid is charged. To the stirred acrolein is gradually added 646 parts by weight of 99.2% isocyanuric acid, to form a slurry. Another 500 parts by weight of acrolein is added to the stirred slurry, followed by 26 parts by weight of acrolein containing 2.4 parts by weight of triethylamine and 1.1 parts by weight of 90% formic acid dissolved therein. The isocyanuric acid contains 0.2 weight percent ammelide- and ammeline-sulfamic acids.

The kettle is sealed, and the stirred reactants are heated gradually to 90° C. over a 25-minute period. An exotherm occurs at about 90° C.; the initial reaction pressure is 170–210 kPa. Reaction temperature is controlled between 89°–91° C. by steady cooling through the cooling coils of the kettle. Controlled reaction is maintained at 89°–91° C. for a total of 45 minutes. However, after 35–40 minutes of reaction, a noticeable decrease in the exothermic rate is observed via the decreased amount of cooling required. The final reaction pressure is about 35 kPa.

After 45 minutes at 90° C., the reaction is terminated by cooling rapidly. Simultaneously 1500 parts of methyl ethyl ketone containing 5 parts of 90% formic acid is pumped into the stirred contents and stirring is continued with cooling until the temperature is ~20° C.

The reaction solution is drained from the kettle. It is filtered once through a Celite bed on a Buchner funnel; and twice through filter paper on a Buchner funnel. To the clear yellow filtrate then is added 15.0 parts of oxalic acid and the solution is stripped in a rotating evaporator at a water bath temperature of 60° C. and an absolute pressure of 120 to 200 mm Hg. When the solvent has been removed by distillation, 800 parts of fresh methyl ethyl ketone is added to dissolve the product. The same stripping procedure is followed. At the end of the second stripping operation, the bath temperature is raised rapidly to 100° C. and maintained at that temperature for about 5 minutes. The residual product, a turbid viscous liquid of 3500 cps viscosity at 80° C., then is mixed with 1500 parts of water and the solution is stripped at 105° C./180-18 mm/30 min. to produce the product. This washing procedure is repeated twice more. The final product is poured into an aluminum tray. When allowed to cool to room temperature, it rapidly hardens to a glassy solid which crystallizes or becomes opaque after 1-48 hours. 1506 parts by weight of product are obtained corresponding to a yield of 100%. The opaque white, glassy solid can be ground up to a white powder. The ratio of aldehyde carbonyl infrared absorbance at 1740 cm$^{-1}$ to isocyanurate absorbance at 780 cm$^{-1}$ is 1.8. The aldehyde content determined by the quantitative hydroxylamine method corresponds to an equivalent weight of 101.6. The residual acrolein monomer, determined by gas chromatography is less than 100 parts per million of product.

When the reaction product is subjected to thin layer chromatography by the general procedure described in Egon Stahl's "Thin Layer Chromatography", Springer-Verlay, Heidelberg-New York, 2nd Ed. 1969 (English Translation) on EM Silica Gel-60-F-254 with ethyl acetate elution (2x) and visualizations by means of UV light (254 nm) for double bonds; dichlorofluorescein; AHTT aldehyde detection agent; and a solution of chlorine in o-toluidine for NH and NH$_2$ detection, four aldehyde components, 1 major corresponding to tris (3-oxopropyl)isocyanurate and 3 lesser, are separated. Two of the lesser ones may be polymeric. A trace of a fifth component, possibly acrolein oligomer, is also observed.

The method of Example 1 is repeated several times and the reaction products are subjected to analysis by a gel permeation chromatography technique. This method employs two Varian Micropak ® TSK columns (sizes 1000H and 2000H in sequence, each 50 cm in length) which can separate materials by size from 100 to about 10,000 molecular weight. Coupled with a UV spectrophotometer detector set at 220 nm wavelength, a tetrahydrofuran solution of the products is separated into 13 components. These consist of 3 groups; polymeric species, isocyanuric acid-acrolein adducts, and acrolein oligomers. Peak height ratios are used to determine relative percentages of the components. The following range is obtained:

monomeric isocyanuric-acrolein adducts: 39–62%
polymer component: 39–58%
acrolein oligomers: 0.3–3.9%

The range of tris-, bis- and mono-(3-oxopropyl)isocyanurates in the monomeric component are determined to be:

tris-(3-oxopropyl)isocyanurate: 39–71%
bis-(3-oxopropyl)isocyanurate: 21–49%
mono-(3-oxopropyl)isocyanurate: 4–14%

The precision of the analysis for the monomeric and polymeric components is ±4%.

$^{13}$C NMR analysis of the reaction product displays the following peaks:

| Peak (ppm) | Assignment |
|---|---|
| 200 | saturated aldehyde carbonyl |
| 148 | isocyanuric acid carbonyl |
| 40.4 | α-methylene of saturated aldehyde |
| 35.8 | methylene attached to ring nitrogen |

Quantitatively, $^{13}$C NMR has measured ranges of 2.0 to 2.7 aldehydes per isocyanuric acid ring.

EXAMPLE 2

Preparation of a Tris(3,3-dimethoxypropyl)isocyanurate Composition

To a kettle equipped with stirrer, thermometer, reflux condenser and holding tank, there is charged 143 parts by weight of the adduct of acrolein and isocyanuric acid of example 1 and 46 parts by weight of methanol. The mixture is warmed until a clear solution of the hemiacetal forms. An additional 142 parts methanol and 125 parts of toluene is charged and is followed by 187 parts methanol containing 3 parts p-toluenesulfonic acid monohydrate. The reaction solution is refluxed for one hour, and 400 parts of solvent containing 14.4 parts of water is then removed by distillation. A mixture of 375 parts of methanol and 125 parts of toluene is added again, and the reaction solution is refluxed for 20 minutes and distilled to remove another 8.8 parts of water. The preceding step is again repeated, and a final 2.9 parts of water is removed. Total water of reaction is 100% of theoretical. The reaction solution is cooled to room temperature and 2.36 parts of calcium hydroxide is added. After 20 minutes of stirring, the slurry is filtered, and the filtrate is stripped under reduced pressure to remove the solvent. The oily residue is dissolved in dry toluene, filtered and again stripped under reduced pressure. 207 g. of crude tris(3,3-dimethoxypropyl) isocyanurate, corresponding to 99% yield, is obtained as a viscous, clear, dark red liquid which solidifies to a tan waxy solid, mp 45°–52° C. The aldehyde content is 2.1 percent of the initial aldehyde content calculated for 100 percent tris(3-oxopropyl)isocyanurate starting material. The infrared spectrum of the product has a strong acetal peak at 1140 cm$^{-1}$.

When the crude tris(3,3-dimethoxypropyl)isocyanurate is suspended in an equal weight of water containing 5% p-toluenesulfonic acid and the slurry is heated at 60° C. for 10 minutes, a clear solution is obtained and the crude tris(3,3-dimethoxypropyl)isocyanurate is converted back to crude tris(3-oxypropyl)isocyanurate. The infrared spectrum now includes an aldehyde carbonyl bond approximately equal in intensity to the aldehyde carbonyl bond of the initial tris(3-oxopropyl)isocyanurate mixture.

EXAMPLE 3

Preparation of a Tris(3-hydroxy-3-methoxypropyl)isocyanurate Composition

An adduct of acrolein and isocyanuric acid is prepared by the method of example 1, except that methyl alcohol is substituted for methyl ethyl ketone, and the filtered solution is vacuum dried at 25° C. over phosphorous pentoxide to constant weight. An infrared spectrum showing a strong hydroxyl band and the almost complete disappearance of the aldehyde carbonyl band at 1740 cm$^{-1}$ confirms the conversion of the polyaldehyde substantially to tris(3-hydroxy-3-methoxypropyl)isocyanurate.

EXAMPLE 4

Preparation of Isocyanuric Monoaldehyde

In a 250 cc. stainless steel bomb, 15.0 parts of 99.2% pure isocyanuric acid, 6.9 parts of freshly distilled acrolein stabilized as in example 1 and 0.15 parts of triethylamine combined with 0.07 parts of 90% formic acid are dissolved in 50 parts of dimethylformamide. The sealed contents then are heated with agitation at 90° C. for 45 min. The cylinder is removed from the bath, cooled in ice to room temperature, and the reaction is filtered through a Buchner funnel. Two percent of an insoluble solid is collected.

The filtrate is stripped of volatiles at room temperature and a pressure of 5 mm Hg. over $P_2O_5$ for 18 hrs., until no more volatiles are collected. Reaction conversion is 98%. By carbonyl analysis using hydroxylamine, the solid product possesses 42% of theoretical maximum value of 3, or an average of 1.3 acrolein per ring. However, thin layer chromatography indicates that the product is a mixture of all three homologues, but that the mono-aldehyde is the major component present.

EXAMPLE 5

Preparation of Isocyanuric Dialdehyde

Under the same conditions described in example 4, a mixture of 15.0 parts of 99.2% pure isocyanuric acid, 13.8 parts of freshly distilled acrolein, 0.17 parts of triethylamine combined with 0.07 parts of 90% formic acid and 50 parts of dimethylformamide are allowed to react. Thin layer chromatography indicates that the product isolated is a mixture of all three homologues but that the dialdehyde is the major component present.

EXAMPLE 6

Preparation of Hemiacetal Solutions

An adduct of acrolein and isocyanuric acid prepared as set forth in example 1 (143 parts by weight) is heated at 50°–60° C. with 46 parts by weight of methanol until a clear homogeneous liquid forms. The liquid is dried under vacuum at room temperature over phosphorous pentoxide for 2 hours. Infrared analysis of the liquid shows a strong hydroxyl band and a weak aldehyde carbonyl band.

Similarly, solutions of the acrolein-isocyanuric acid adduct are prepared by reaction of the aldehyde with isopropyl alcohol, n-butyl alcohol, 2-ethylhexanol-1, and benzyl alcohol. The infrared absorption band for aldehyde carbonyl in these products also is significantly less intense than the aldehyde band in the initial acrolein-isocyanuric acid adduct. The aldehyde carbonyl band is less intense in the spectra of hemiacetal products of the higher boiling alcohols in comparison with the hemiacetal products of the lower boiling alcohols, suggesting that the equilibrium is less readily shifted back to the aldehyde because of the lower volatility of such alcohols.

Little reaction is observed between t-butyl alcohol and the tris(3-oxopropyl)isocyanurate material. The latter did not go into solution in t-butyl alcohol even after prolonged heating at 80° C.

EXAMPLE 7

Preparation of Polyol from Adipic Acid and Trimethylolpropane

To a kettle equipped with a stirrer, condenser with water trap, thermometer and holding tank, 805 parts of trimethylolpropane, 438 parts of adipic acid, 173 parts of toluene and 7.5 parts of stannous octoate are charged and refluxed at a temperature of 118° C. rising to 133° C., until the theoretical amount of water is collected. The reaction time is 10.75 hr. 108 parts of water is collected in the trap. (theoretical 108).

To the final product at 60° C., 750 parts of methanol is added from the holding tank. The resulting solution is filtered and the filtrate is stripped of volatiles by vacuum distillation.

The product weight is 1135 parts, corresponding to 100 percent yield.

The product is a clear, light yellow, viscous oily liquid. The acidity is 0.082 meq acid per gram. The viscosity is 20,000 cps. at 25° C.

EXAMPLE 8

Polyol Coating Composition

A coating composition is prepared by blending 36.9 parts of the polyol of example 7, 24.6 parts of the aldehyde reaction product of example 1, 0.1 parts of trifluoromethanesulfonic acid, 1.2 parts of a fluorocarbon surfactant sold by 3M Co. under the tradename FC-430, 0.6 parts of an ultraviolet stabilizer sold by American Cyanamid Company under the tradename UV 9, 0.2 parts of 2,6-di-t-butyl-4-methylphenol, 24 parts of methanol and 12.3 parts of cellosolve acetate. The solids content of the blend is 63.7% and the viscosity is 140 cps at 25° C. The blend is coated onto steel panels and dried to give a coating thickness of 1.3 mils. The coating is cured at 107° C. for 30 minutes. A hard, glossy solvent-resistant and impact-resistant coating is obtained.

EXAMPLE 9

Polyepoxide Coating Composition

A coating composition is prepared by blending 57.6 parts of an aliphatic diepoxide sold by Union Carbide Corporation under the tradename ERL-4299, 24.7 parts of the aldehyde reaction product of example 1, 0.1 parts of boron trifluoride etherate, 0.2 parts of a fluorocarbon surfactant sold by 3M Co. under the tradename FC-430, 10.7 parts of methyl ethyl ketone, and 6.7 parts of methyl alcohol. The solids content of the blend is 82.7%. The viscosity is 440 cps. The blend is coated onto steel panels and dried to give a coating thickness of 1.5 mil. After cure at 150° C. for 30 minutes, a hard, glossy, solent- and impact-resistant coating is obtained.

EXAMPLE 10

Polyepoxide Coating Composition

A coating composition is prepared by blending 58 parts of an aliphatic diepoxide sold by Union Carbide Corporation under the tradename ERL-4299, 25 parts of the reaction product of example 1, 11 parts of endo-cis-bicyclo (2,2,1)-7-methyl-5-heptene-2,3-dicarboxylic anhydride, 5 parts of tetrabutylphosphonium chloride and 2 parts of a fluorocarbon surfactant sold by 3M Co. under the tradename FC-430. The solids content of the blend is 100 percent and the viscosity is 3500 cps at 25° C. The blend is coated on steel panels and cured at 120° C. for 30 minutes. The cured coating is hard, glossy, solvent- and impact-resistant.

EXAMPLE 11

Starch Coating Crosslinked by Isocyanuric Trialdehyde

The following formulation is prepared by combining a solution of (a+b) with a solution of (c+d) and adding e:

| | | |
|---|---|---|
| a. | Starch | 9.8 pts by weight |
| b. | Water | 87.7 pts |
| c. | Acrolein-isocyanuric acid adduct of example 1 | 1.6 pts (14% on starch) |
| d. | Methanol | 0.7 pts |
| e. | Trifluoromethanesulfonic Acid | 0.2 pts |
| | Total | 100.0 pts |

The 11.6 percent solids solution is coated on a steel panel and baked at 250° F. for 30 min. The resulting nonglossy coating softens slightly but resists attack by water.

EXAMPLE 12

Polyvinyl Alcohol Cross Linked by Isocyanuric Trialdehyde

The following formulation is prepared by combining a solution of (a+b) with a solution of (c+d) and adding e:

| | | |
|---|---|---|
| a. | Polyvinyl Alcohol | 48.1 pts by weight |
| b. | Water | 36.9 pts |
| c. | Acrolein-isocyanuric acid adduct of example 1 | 8.5 pts (15% on PVOH) |
| d. | Methanol | 4.8 pts |
| e. | Fluosulfonic Acid (FSO$_3$H) | 1.7 pts |
| | Total | 100.0 pts |

The polyvinyl alcohol has a weight average molecular weight of 2000 and contains 40 weight percent of vinyl acetate units. The 58.3 percent solids solution is coated on steel panels and baked at 250° F. for 30 min. The resulting yellow coating is non-glossy, hard, water-insoluble and impact resistant.

EXAMPLE 13

Hydrolyzed Ethylene-Vinyl Acetate Polymer Coating Cured by Isocyanuric Trialdehyde The following formulation is prepared:

| | | |
|---|---|---|
| a. | Hydrolyzed Ethylene-Vinyl Acetate Copolymer | 31.0 pts by weight |
| b. | 2-Methoxyethyl acetate | 12.4 pts |
| c. | Acrolein-isocyanuric acid adduct of example 1 (50% on EVOH) | 31.0 pts |
| d. | Methanol | 24.1 pts |
| e. | Flourinated Surfactant FC-430 (supplied by 3 M Co.) | 1.5 pts |
| f. | Trifluoromethanesulfonic Acid | 0.03 pts |
| | Total | 100.0 pts |

The hydrolyzed ethylene-vinyl acetate copolymer contains 70 weight percent ethylene units, 24 weight percent vinyl alcohol units and 6 weight percent vinyl acetate units. The 63.5 percent solids solution is coated on steel panels and baked at 300° F. for 30 min. The resulting yellow coating is non-glossy, impact-resistant and insoluble in methyl ethyl ketone.

EXAMPLE 14

Terpolymer (Methyl Methacrylate-Ethyl Acrylate-Monoallyl Ether of Trimethylolpropane) Coating Cured by Isocyanuric Trialdehyde The following formulation is prepared:

| | | |
|---|---|---|
| a. | MMA-EA-ATMP Terpolymer (containing 8.54 weight percent hydroxy content) | 27.3 pts by weight |
| b. | Acrolein-isocyanuric acid adduct of example 1 (24% on terpolymer) | 8.6 pts. |
| c. | Acetone | 55.4 pts. |
| d. | Cyclohexanone | 8.6 pts. |
| e. | Fluorinated Surfactant FC-430 | 0.03 pts. |
| f. | Trifluoromethanesulfonic Acid | 0.04 pts. |
| | Total | 100.0 pts. |

The 36 percent solids solution is coated on steel panels and baked at 300° F. for 30 min. The resulting dark yellow coating resists attack by methyl ethyl ketone without softening.

EXAMPLE 15

Polyol Coating Cured by Isocyanuric Trialdehyde

The following formulation is prepared:

| | | |
|---|---|---|
| a. | Polyol | 30.9 pts. |
| b. | Adduct of acrolein and isocyanuric acid, example 1 | 15.5 pts. |
| c. | Acetone | 53.6 pts. |
| d. | Fluorinated Surfactant FC-430 | 0.03 pts. |
| e. | Trifluoromethanesulfonic Acid | 0.02 pts. |
| | Total | 100.0 pts. |

The polyol is the diglycol obtained by hydrolysis of the diglycidyl ether of hydrogenated bisphenol-A. The 46.4 percent solids solution is coated on steel panels and baked at 225° F. for 30 min. The resulting coating is humidity- and solvent-resistant.

EXAMPLE 16

Reaction of Polyamines with Isocyanuric Trialdehyde

The following polyamines are reacted with the acrolein-isocyanuric acid adduct of example 1.

Structure

-continued

Structure

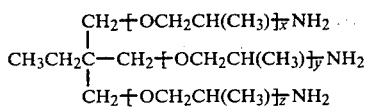

$x + y + z = 5.3$ 30 parts by weight of the isocyanuric-acrolein adduct is mixed with 70 parts by weight of each of these amines at room temperature. Immediate gelation and color formation occurs.

EXAMPLE 17

Polyepoxide Casting Composition

The following composition is prepared:

| (a) | Diglycidyl Ether of Bisphenol-A | 48.6 pts. |
|---|---|---|
| (b) | Acrolein-isocyanuric acid adduct of example 1. | 48.6 pts. |
| (c) | Tetrabutylphosphonium Acid Acetate | 2.8 pts. |
| | Total | 100.0 pts. |

The clear mixture is poured at room temperature into a Telfon ®-lined tray and heated in an oven at 150° F. for 60 min., followed by 200° F. for 60 min. Specimens of the resulting thermoset casting display good tensile and flexural properties.

EXAMPLE 18

Polyol Casting Composition

The following composition is prepared at 135° C.:

| (a) | Ester product of 1 mole adipic acid and 2 moles trimethylolpropane (Example 7) | 45 pts. |
|---|---|---|
| (b) | Ester product of 1 mole terephthalic acid and 2 moles trimethylolpropane | 5 pts. |
| (c) | Acrolein-isocyanuric acid adduct of example 1 | 50 pts. |
| | Total | 100.0 pts. |

The molten product is poured into a Telfon ®-lined tray and allowed to cool to room temperature. Specimens of the resulting thermoplastic casting display good tensile, flexural and impact properties.

EXAMPLE 19

Polyol Casting Composition

The following composition is mixed at 125° C.;

| (a) | Ester product of 1 mole azelaic acid and 2 moles trimethylolpropane | 32.5 pts. |
|---|---|---|
| (b) | Styrene-Allyl Alcohol copolymer | 32.5 pts. |
| (c) | Acrolein-isocyanuric acid adduct of Example 1 | 35 pts. |
| | Total | 100.0 pts. |

The styrene-allyl alcohol copolymer has a molecular weight of 1150 and hydroxyl content of 7.7% and is sold by Monsanto under the registered trademark RJ-101. The molten product is poured into a Teflon ®-lined tray and allowed to cool to room temperature. Specimens of the resulting thermoplastic casting display good tensile and flexural properties.

EXAMPLE 20

Polyamide Coating Composition

The following coating formulation is prepared:

|   |   | Wt (pts) |
|---|---|---|
| (a) | Acrolein-isocyanuric acid adduct of Example 1 | 15.7 |
| (b) | Dimer Acid Diamide | 36.9 |
| (c) | Methanol | 18.8 |
| (d) | Methyl Ethyl Ketone | 27.7 |
| (e) | Fluorad FC-430 | 0.3 |
| (f) | p-Toluenesulfonic Acid | 0.65 |
| | Total | 100.1 |

The 53.5 percent solids solution is coated on steel panels and baked at 72° C. for 30 minutes. The resulting clear, light-brown, glossy coating is tough, water resistant and insoluble in methyl ethyl ketone.

What is claimed is:

1. A composition comprising a polyfunctional hemiacetal-reactive compound and a hemiacetal of a monohydric primary or secondary alcohol and an acrolein-isocyanuric acid adduct.

2. The composition of claim 1 wherein the adduct comprises from about 1 to about 3 moles of acrolein added per mole of isocyanuric acid and is hemiacetalized with from about 0.5 to about 1 mole of monohydric alcohol per mole of combined acrolein.

3. The composition of claim 2 wherein the monohydric alcohol is a $C_1$ to $C_8$ alcohol.

4. The composition of claim 2 wherein the monohydric alcohol is methyl alcohol.

5. The composition of claim 1, 2, 3 or 4 wherein the mole ratio of hemiacetal to polyfunctional hemiacetal-reactive compound is in the range of about $1:m/2$ to about $n/2:1$ where m is the functionality of the hemiacetal and n is the functionality of the polyfunctional hemiacetal-reactive compound and m and n are at least about 2.

6. The composition of claim 5 wherein the functional groups of the hemiacetal-reactive compound are selected from the group consisting of primary and secondary amine, primary and secondary amide, alcohol, thiol and oxirane.

7. The composition of claim 5 wherein the hemiacetal-reactive compound is a polyhydroxy compound.

8. The reaction product of the composition of claim 5.

9. The reaction product of the composition of claim 6.

10. The reaction product of the composition of claim 7.

11. An article comprising the reaction product of the composition of claim 5.

12. An article comprising the reaction product of the composition of claim 6.

13. An article comprising the reaction product of the composition of claim 7.

* * * * *